United States Patent
Behl

(10) Patent No.: US 6,471,695 B1
(45) Date of Patent: Oct. 29, 2002

(54) APPARATUS AND METHOD FOR SHIELDING TISSUE DURING TUMOR ABLATION

(75) Inventor: Robert S. Behl, Palo Alto, CA (US)

(73) Assignee: Radiotherapeutics, Inc., San Jose, CA (US)

( * ) Notice: Subject to any disclaimer, the term of this patent is extended or adjusted under 35 U.S.C. 154(b) by 0 days.

(21) Appl. No.: 09/656,307

(22) Filed: Sep. 6, 2000

(51) Int. Cl.$^7$ .............................................. A61B 5/0408
(52) U.S. Cl. .................. 606/32; 600/373; 600/382; 607/152; 128/850
(58) Field of Search ................................. 128/908, 918, 128/849, 850, 852; 607/156; 606/32, 33, 38, 34, 41

(56) References Cited

U.S. PATENT DOCUMENTS

| | | |
|---|---|---|
| 3,991,770 A | 11/1976 | LeVeen |
| 4,016,886 A | 4/1977 | Doss et al. |
| 4,140,130 A | 2/1979 | Storm III |
| 4,186,729 A | 2/1980 | Harrison |
| 4,448,198 A | 5/1984 | Turner |
| 4,520,814 A * | 6/1985 | Weeks .......................... 128/850 |
| RE32,066 E | 1/1986 | LeVeen |
| 4,651,734 A | 3/1987 | Doss et al. |
| 4,901,738 A * | 2/1990 | Brink et al. ................. 128/850 |
| 4,969,468 A | 11/1990 | Byers et al. |
| 5,225,236 A * | 7/1993 | Keusch et al. ............... 128/850 |
| 5,381,802 A * | 1/1995 | Schwartzenfeld ........... 128/899 |

(List continued on next page.)

FOREIGN PATENT DOCUMENTS

| | | |
|---|---|---|
| DE | 2 124 684 | 11/1972 |
| WO | WO 96/29946 | 10/1996 |
| WO | WO 97/06739 | 2/1997 |
| WO | WO 97/06740 | 2/1997 |
| WO | WO 97/06855 | 2/1997 |
| WO | WO 97/06857 | 2/1997 |
| WO | WO 98/52480 | 11/1998 |
| WO | WO 99/0410 | 1/1999 |
| WO | WO/99/32041 | 7/1999 |

OTHER PUBLICATIONS

Rockwell, "The Medical Uses of Electricity", E.B. Trent & Co., New York, NY p.558 (1903).
Radio Therapeutics Corporation Brochure (002), LeVeen™ Needle Electrode (1998).

*Primary Examiner*—Linda C. M. Dvorak
*Assistant Examiner*—David M. Ruddy
(74) *Attorney, Agent, or Firm*—Townsend and Townsend and Crew LLP

(57) ABSTRACT

The present invention provides improved methods, systems, and kits for protecting body tissues which are adjacent to tissues undergoing thermal treatment. Thermal treatment is often prescribed for tumors and other disease conditions within body organs and other tissue masses. The methods, systems, and kits are particularly useful for treating tumors which lie at or near the surface of an organ, such as the kidney, pancreas, stomach, spleen, and particularly the liver. One risk of treating such tumors is the possibility of mistargeting the tumor and penetrating a delivery cannula or portions of a treatment device beyond the surface into the adjacent tissues or organs. In the case of radiofrequency or electrosurgical treatment, healthy surrounding tissue may be directly ablated. An additional risk, present even when the tumor is correctly targeted, is the possibility of thermal damage to the surrounding, non-targeted tissue. In radiofrequency or electrosurgical treatment, heat may dissipate into surrounding tissues which are more fragile and heat sensitive than the tissue in the organ being treated, thus causing unwanted tissue damage. These risks and others may be lessened or avoided with the use of an interface shield between the target region and adjacent body tissues to shield surrounding organs and tissue from treatment effects.

89 Claims, 5 Drawing Sheets

U.S. PATENT DOCUMENTS

| | | |
|---|---|---|
| 5,472,441 A | 12/1995 | Edwards et al. |
| 5,536,267 A | 7/1996 | Edwards et al. |
| 5,720,743 A * | 2/1998 | Bischof et al. ............... 606/1 |
| 5,728,143 A | 3/1998 | Gough et al. |
| 5,766,165 A | 6/1998 | Gentella et al. |
| 5,827,276 A | 10/1998 | LeVeen et al. |
| 5,855,576 A | 1/1999 | LeVeen et al. |
| 5,868,740 A | 2/1999 | LeVeen et al. |
| 5,885,277 A | 3/1999 | Korth |
| 6,050,992 A | 4/2000 | Nichols |
| 6,081,749 A | 6/2000 | Ingle et al. |
| 6,312,426 B1 * | 11/2001 | Goldberg et al. ............. 606/33 |

* cited by examiner

APPARATUS AND METHOD FOR SHIELDING TISSUE DURING TUMOR ABLATION

BACKGROUND OF THE INVENTION

1. Field of the Invention

The present invention relates generally to methods, apparatus and kits used for protecting a body tissue which is adjacent to a target tissue undergoing thermal treatment. Particularly, the present invention relates to the protection of the adjacent body tissue from penetration and/or thermal effects by a tissue penetrating thermal device. More particularly, the present invention relates to an interface shield used to protect body tissue adjacent to target tissue from the possible effects of using a radiofrequency electrosurgical apparatus to treat tumors in the target tissue.

The delivery of radiofrequency energy to target regions or target tissues within solid tissue is known for a variety of purposes. Of particular interest to the present invention, radiofrequency energy may be delivered to diseased regions in target tissue for the purpose of causing tissue necrosis. For example, the liver is a common depository for metastases of many primary cancers, such as cancers of the stomach, bowel, pancreas, kidney, and lung. Electrosurgical probes for deploying multiple electrodes have been designed for the treatment and necrosis of tumors in the liver and other solid tissues. See, for example, the LeVeen™ Needle Electrode available from Radio Therapeutics Corporation which is constructed generally in accord with U.S. Pat. Nos. 5,858, 740; 5,855,576; 5,827,276 and international patents WO 96/29946 and WO 98/52480. The probes described in these patents comprise a number of independent wire electrodes which are extended into tissue from the distal end of a cannula. The wire electrodes may then be energized in a monopolar or bipolar fashion to heat and necrose tissue within a defined volumetric region of target tissue. In general, the larger the volume treated, the more wire electrodes are necessary to ensure homogeneity of treatment.

Of particular interest to the present invention, as recognized by the inventor herein, use of the multiple electrode arrangements in treating tumors which lay near an adjacent tissue structure requires particular care. For example, as illustrated in FIG. 1, a tumor T deep in the liver LVR may be close to a back or side surface S of the organ, adjacent to the diaphragm D and/or surrounding lung LNG. It may be desirable to access such a tumor T through an entry site E which is opposite this surface S, or at a location which is a considerable distance away from this surface S. A needle electrode 10 may be inserted through the entry point E, traverse healthy liver LVR tissue and be placed within or near the tumor T to be treated. However, if the tumor T is mistargeted, the needle electrode 10 may be misplaced, allowing the electrode tips 12 to protrude and traverse the surface S. Thus, the tip of the needle electrode 10 or the subsequently deployed electrode tips 12 may punch into or through the diaphragm D and possibly into the lung LNG. Such exposure of the electrode 10 or needle tips 12 outside of the liver LVR is disadvantageous in a number of respects. Beyond simple puncture damage, the presence of active electrodes outside of the confinement of the organ being treated subjects other tissue structures of the patient as well as the treating personnel to risk of accidental contact with the electrodes. This may directly destroy healthy tissue in the surrounding organs and tissues or it may cause heat damage. Moreover, the presence of all or portions of particular electrodes outside of the tissue being treated can interfere with proper heating of the target tissue and fail to destroy all or part of the tumor.

As illustrated in FIG. 2, a tumor T in a similar location near a surface S may likewise be accessed through an entry point E which is opposite to this surface S. Even if the tumor T is not mistargeted and the needle electrodes are properly placed within the tumor T such that they do not protrude outside of the liver LVR, surrounding tissue may still be damaged. Heat emanating from the tissue surrounding the electrode tips 12 may raise the temperature of additional non target tissues within a given radius via conduction, as illustrated by a dashed outlined area A. Some tissue in area A may be more fragile or thermally sensitive than the target tissue being treated. Thus, such tissue may be raised to a damaging or lethal temperature during the treatment of a surface tumor in an adjacent organ.

Electrosurgical treatment of such tumors within body organs often involves applying radiofrequency energy in a monopolar fashion where the treatment current travels between the treatment electrode and a dispersive or counter electrode disposed on the patient's skin. Such an electrode deployment is designed to disperse the energy, as much as possible, as distance increases from the treatment electrode in order to avoid local heating in unwanted locations. This is typically accomplished by designing the dispersive electrode to have a much larger surface area relative to the treatment electrode so that the current density is rapidly dispersed over a correspondingly larger area of tissue. However, despite proper surface area ratios of the treatment electrode to the dispersive electrode, placement of such a dispersive electrode on the outside of the patient's body may not optimally direct the dispersed energy flow through the tissues surrounding those targeted for treatment. Current flow will follow the path of minimal resistance, partly determined by the shortest distance between the treatment and dispersive electrodes. Thus, sufficient energy delivery to the treatment site may also inadvertently damage healthy tissue located between the treatment site and the dispersive electrode on the outside of the body.

For all of these reasons, it would be desirable to provide improved methods and systems for treating tumors within an organ or tissue, particularly those located adjacent to other tissue structures which are at risk of injury. It would be further desirable to provide such improved methods and systems which would protect surrounding tissue from thermal damage. It would also be particularly desirable if such methods and systems could lessen the risk of accidental penetration of a treatment device into adjacent tissue structures. It would be further desirable if the methods and systems could enhance and make more predictable the uniform treatment of the entire tumor mass, including those portions which lie near the surface of the organ being treated. Finally, it would be desirable to avoid excessive heating and the passage of excessive current through non-target tissues by providing the shortest path between active and dispersive electrodes. At least some of these objectives will be met by the invention of the present application.

2. Description of the Background Art

U.S. Pat. Nos. 5,868,740; 5,855,576; 5,827,276 and international patents WO 96/29946 and WO 98/52480 describe an electrosurgical probe having deployable electrode elements of the type described above. The LeVeen™ Needle Electrode constructed in accordance with the teachings of the above named patents is available from Radio Therapeutics Corporation, assignee of the present application, and is illustrated in brochure RTC 002 published in 1998. Other electrosurgical devices having deployable electrodes are described in German Patent 2124684 (Stadelmayr); U.S. Pat. No. 5,472,441 (Edwards et al.); U.S. Pat. No. 5,536,267 (Edwards et al.); U.S. Pat. No. 5,728,143 (Gough et al.); and U.S. Pat. No. 6,050,992 (Nichols); and PCT Publications WO 97/06739; WO 97/06740; WO 97/06855; and WO 97/06857. Medical electrodes having pins and other structures are shown in U.S. Pat. Nos. 3,991,770; Re. 32,066; 4,016,886; 4,140,130; 4,186,729; 4,448,198; 4,651,734; and 4,969,468. A skin surface treatment electrode for the removal of blemishes having a circular array of tissue-penetrating pins is described in Rockwell, The Medical and Surgical Uses of Electricity, E. B. Trent & Co., New York, 1903, at page 558. A cluster electrode comprising a plurality of electrodes projecting from a plate for insertion in tissue is described in WO 99/0410. Another patent of interest includes WO 99/32041 (Kamdar et al).

SUMMARY OF THE INVENTION

The present invention provides improved methods, systems, and kits for protecting body tissues which are adjacent to tissues undergoing thermal treatment. Thermal treatment is often prescribed for tumors and other disease conditions within body organs and other tissue masses. The methods, systems, and kits are particularly useful for treating tumors which lie at or near the surface of an organ, such as the kidney, pancreas, stomach, spleen, uterus and particularly the liver. In some situations, such tumors may not be easily accessible through the surface of the organ closest to which they are located. This may be the case when tumors or located along back or side walls of an organ. Thus, it may be desirable to access the tumor through a wall or surface of the organ which is opposite or at a distance from the tumor. One risk of treating such tumors in this manner is the possibility of mistargeting the tumor and penetrating a delivery cannula or portions of a treatment device beyond the surface into the adjacent tissues or organs. In the case of treating the liver, adjacent tissues will most likely include the diaphragm, lung and/or colon. In the case of treating the kidney or uterus, adjacent tissues will most likely include the colon.

During thermal treatment, healthy surrounding tissue may be inadvertently mistargeted and directly ablated. An additional risk, present even when the tumor is correctly targeted, is the possibility of thermal damage to the surrounding, non-targeted tissue. In thermal treatment, heat may dissipate into surrounding tissues which are more fragile and heat sensitive than the tissue in the organ being treated, thus causing unwanted tissue damage. These risks and others may be lessened or avoided with the use of an interface shield between the target region and adjacent body tissues to shield surrounding organs and tissue from treatment effects.

According to the methods of the present invention, a target region of tissue in an organ may be identified and targeted by various imaging means for thermal treatment. Thermal treatment may include the delivery of various types of energy for hyperthermic and/or hypothermic effects. In one exemplary case, radiofrequency energy may be delivered for hyperthermic therapy. Generated heat may necrose tissue in a given area, forming a lesion. Similarly, laser probes and electric cauterizers/resistance heated probes, to name a few, may be used. Alternatively, hypothermic treatment may be delivered by cryogenic probes, for example. Hereinafter, thermal treatment will primarily be described in terms of hyperthermic treatment and the production of heat. However, it may be appreciated that such terminology is not intended to limit the scope of the present invention. Heat, heat transfer, heat absorption, heat conduction, and similar terminology may be understood to include synonymous situations and conditions in hypothermic treatment.

If a target tissue region is sufficiently close to a surface of the organ in which it is located, it may be desired to provide a conformable temporary interface shield between the organ surface and the adjacent tissue to prevent the treatment from damaging the adjacent tissues. The interface shield may be positioned over the surface such that the shield lies between the target region and adjacent body tissues. In the case of radiofrequency treatment, at least one tissue penetrating electrode may then be introduced to the target region in a direction toward the protective interface shield. Any electrodes or portions of the device which penetrate the surface of the organ will be prevented from entering the surrounding tissue due to the presence of the shield. Once the electrode is positioned in a desired configuration, electrical energy, such as radiofrequency or other high frequency energy, may be applied to the target region of tissue through the electrode. The energy may be applied in a bipolar fashion where current flows between separated portions of the electrode or between two separate electrodes. Alternatively, the energy may be applied in a monopolar fashion where the current flows between the treatment electrode and a dispersive or passive electrode. The dispersive electrode is typically disposed on the patient's skin, however in some cases the protective interface shield may also function as a dispersive electrode as will be further described herein.

In a first aspect of the present invention, the protective interface shield reduces the incidence of at least one of (a) thermal treatment device penetration into adjacent body tissues and (b) heat transfer into adjacent non-targeted body tissues. It may be appreciated that the treatment device may include a delivery device, probe or cannula to position the treatment device in a desired location. The shield is comprised of a flexible planar member having at least a first layer comprising a penetration barrier and a second layer comprising a heat transfer barrier. In the case of electrosurgical treatment, the thermal treatment device may comprise a radiofrequency electrode or needle electrode. In a preferred embodiment, an array of such electrodes may be advanced forwardly from a distal end of a probe or sharpened cannula during placement, so that the electrodes evert outwardly as they are advanced into the target tissue. The penetration barrier may resist penetration by the probe and/or needle electrodes as they are advanced and positioned in the target tissue. Specifically, electrode tips may attempt to penetrate the surface of the organ and advance toward adjacent tissue. However, the penetration barrier may serve to resist tip advancement and/or deflect such a tip in a direction away from the adjacent tissues which are desired to be protected from such treatment. Thus, the penetration barrier may be comprised of any suitable penetration resistant material. Penetration resistance may be measured as toughness by Charpy or Izod according to ASTM D256. Preferred materials have a penetration resistance or toughness equal to or greater than 10 cm-kg/cm (2.0 ft-lbf/in).

Radiofrequency (RF) energy is supplied to the needle electrodes which heat the target tissue for a period of specified time and at a power level sufficient to necrose tissue. Transfer of such heat through the flexible planar member may be reduced by the heat transfer barrier. This may be accomplished with the use of a material which acts as a thermal insulator, providing a passive barrier to conductive heat transfer. Preferred materials may be at least partially hydrophobic or non-hydrophilic so as to maintain such thermal insulation properties in a moist body environment. Such materials may include closed cell or open cell foams. Alternatively, the barrier of heat transfer to adjacent tissue may be accomplished with the use of a material which absorbs heat or acts as a heat sink. Such a heat sink, for example, may provide active cooling as a barrier to heat transfer. This may be provided by a material that can undergo an endothermic phase change or endothermic chemical reaction at or above body temperature. One example of such a material is a frozen medium which melts at body temperature. The frozen medium may be encapsulated in a leak-proof container to prevent loss of medium to the environment. Still further, the heat transfer barrier may be comprised of a material that conducts heat away from the target tissue. This may be accomplished by a metallic sheet. The metallic sheet may preferentially conduct heat away from the tissue targeted with the highest heat concentration. This may be desired to more evenly distribute the generated heat over a wider surface area with increased heat conductivity.

The materials comprising the above described barriers may be arranged in any number of patterns or configurations to comprise the protective interface shield. Such arrangements may include stacked layers or encapsulated layers, to name a few. In some cases, a material may be selected which inhibits both needle penetration and heat transfer for use in constructing the flexible planar member. In such a situation, the first and second layers may be comprised of the same material, essentially forming one layer and providing both functions.

In a second aspect of the present invention, the protective interface shield may provide electrical conductivity, similar to that found in body fluids and tissues. The shield may be comprised of a layer of electrically conductive material in addition to the above described layers and/or functions. Preferred materials may include hydrophilic or at least partially hydrophilic materials. Such a material may comprise a porous substrate capable of absorbing a conductive fluid, such as saline, blood or other body fluids. The electrically conductive layer may be designed to encourage symmetrical dispersion of radiofrequency energy from within the target treatment site. However, it is also desirable that such a layer not be so conductive, as in a metallic layer, so as to cause an undesired preferred current path, leading to lesion asymmetry. To achieve this, the layer should have an electrical conductivity similar to body tissue. In addition, the materials comprising the protective interface shield should be arranged so that the conductive layer is located near the surface of the shield and is placed toward the surface of the target tissue under treatment. It may be appreciated that such a layer may also extend around the interface shield to form an encapsulating layer or jacket.

In a third aspect of the present invention, the protective interface shield may provide a dispersive electrode. The shield may be comprised of a layer providing a dispersive electrode in addition to the above described layers and/or function. As mentioned, when energy is applied to the target tissue in a monopolar fashion, a large dispersive electrode is typically disposed on the patient's skin. However, such placement may not optimally direct energy through the target tissue and may damage healthy tissue in surrounding areas.

Placement of a similar dispersive electrode within the interface shield may provide a number of advantages. First, the shape and location of the lesion created to engulf a tumor or target tissue may be optimized. For example, an asymmetrical lesion may be created to treat a non-spherical tumor or target tissue. Typically, when a dispersive electrode is placed on the patient's skin, relatively remote from the treatment site, the treatment electrode creates a symmetrical or spherical lesion centered about the electrode. Although the current travels between the treatment electrode and the dispersive electrode, distance between the electrodes disperses the current and creates asymmetrical lesion. By utilizing an interface shield having dispersive electrode layer, the treatment current will preferentially travel between the treatment electrode and the close proximity electrode layer within the shield. The resulting lesion will extend toward the shield and will be ellipsoidal or cylindrical, rather than spherical. In some cases, the dispersive electrode layer may eliminate the need for an external dispersive electrode placed on the patient's skin. Second, use of a shield containing a dispersive electrode in combination with one or more standard skin placed dispersive electrodes may result in a higher proportion of the electrical output used to heat tissue in the target region and less energy dissipated into surrounding non-target tissue. Here the dispersive electrode layer, when connected to a current source in parallel with a dispersive electrode on the surface of the body of the patient, may reduce the total impedance of the system so that a higher proportion of the electrical output becomes usable to heat the target tissue.

The dispersive electrode layer comprises a material that provides a higher level of conductivity than either body tissue or any other electrically conductive layer which is part of the shield. This provides a more preferential path for dispersion of applied energy. It is not required that the dispersive electrode layer directly contact body tissue, and in fact such contact would be undesirable. Construction of the dispersive electrode layer in the form of a capacitor may provide a low impedance energy return without the possibility of a "short-circuit" caused by contact with the treatment electrode. Capacitive coupling of the radiofrequency energy to this dispersive electrode tends to spread the RF current over a wider surface than if it were in direct tissue contact. This may allow the user to maintain a higher level of current in the target tissue region while reducing the risk of creating a "hot spot" or increased level of tissue damage between the treatment electrode and the shield surface.

The materials comprising the above described functions may be arranged in a number of patterns or configurations to comprise the protective interface shield. Such arrangements may include stacked layers or encapsulated layers, to name a few. It is preferred that material comprising a heat transfer barrier, as described above, be positioned as a layer between the dispersive electrode layer and the surrounding non-target tissue. Typically, materials which provide a barrier to heat transfer also provide electrical insulation. Thus, such a layer may act to further protect the shielded tissue from both damage due to conducted heat and damage due to radiofrequency current heating. It is preferred that material comprising a dispersive electrode layer, as described above, also be positioned as a layer between the heat transfer barrier and the penetration barrier, both of which being non-conductive will isolate the dispersive electrode from direct tissue contact. Such a shield will typically be positioned in the body so that the above described layers are placed in the following order from the target tissue outward toward the adjacent non-target tissue: penetration barrier, dispersive electrode layer, heat transfer barrier. This may protect the dispersive electrode layer from the possibility of penetration or contact by the treatment electrode placed within the target tissue, and may simultaneously protect the adjacent non-target tissue from excessive thermal damage. A conductive layer, described previously, may also be present between the penetration barrier and target tissue or fully encapsulating the shield, however it is not essential in this configuration.

In a fourth aspect of the present invention, the protective interface shield may have a surface finish, coating or layer to provide desired surface characteristics for specific purposes. Such a surface layer may be non-sliding to minimize movement between the shield and the contacting tissue. This may be useful when placed against the target tissue organ to retain the shield in position. Suitable materials may include a gauze or a felt. Alternatively, the surface layer may be slippery or provide a low friction interface between the shield and the contacting tissue. This may be useful for contact against adjacent tissues which may move relative to the shield so that such tissues may slide with reduced irritation or frictional damage. In a preferred embodiment, an interface shield may be comprised of a surface layer on each side of the planar member with opposite characteristics, e.g. with a non-sliding surface against a stationary target organ such as the liver, and a low friction surface against an adjacent tissue such as the diaphragm, which moves with respiration. The above described surface characteristics may also be provided by any of the previously described layers of the interface shield providing functions related to other aspects of the present invention. For example, the conductive layer has been described as being located on the surface of the interface shield to be placed against the target tissue. This layer may be comprised of a rough textured hydrophilic fabric which may also serve as non-sliding surface coating to hold the shield in position. Likewise, the heat transfer barrier has been described as being located on the surface of the interface shield, particularly for placement against the adjacent, non-targeted tissue. The heat transfer barrier may be comprised of a material which enhances movement between the shield and the adjacent tissue, such as a smooth polyethylene foam or a heat absorbing or conducting material coated with a hydrophilic material. Thus, surface layers may be multi-functional.

In addition, it may be appreciated that multiple interface shields may be used during treatment of a target tissue. It may be desired to position one shield over the surface of the target tissue to protect adjacent tissue. At the same time, shields may also be positioned over tissues that are not immediately adjacent the surface of the target tissue but are within an area of the target tissue that may be injured from the thermal treatment. This may provided added protection for surrounding tissues, specifically particularly susceptible or sensitive tissues. Such individual shields may have an area in the range from 50 cm$^2$ to 300 cm$^2$. It is also possible to use more than one shield in any given location, such as in a stacked configuration, to provide possibly additional protective effects, or by interlocking with adjacent shields to protect additional contiguous tissue area.

The methods and devices of the present invention may be provided in one or more kits for such use. The kits may comprise at least one interface shield and instructions for use. Optionally, such kits may further include additional shields. Each shield may be designed for placement in specific locations, for contact with specific tissues or to provide specific functions. Alternatively, a number of shields may be provided for positioning in numerous locations; such shields may be capable of interlocking to cover a larger surface area, or they may be stacked or layered in one location. Optionally, such kits may further include a tissue penetrating electrode and any other materials or items relevant to the present invention.

DESCRIPTION OF THE SPECIFIC EMBODIMENTS

Figure 3:
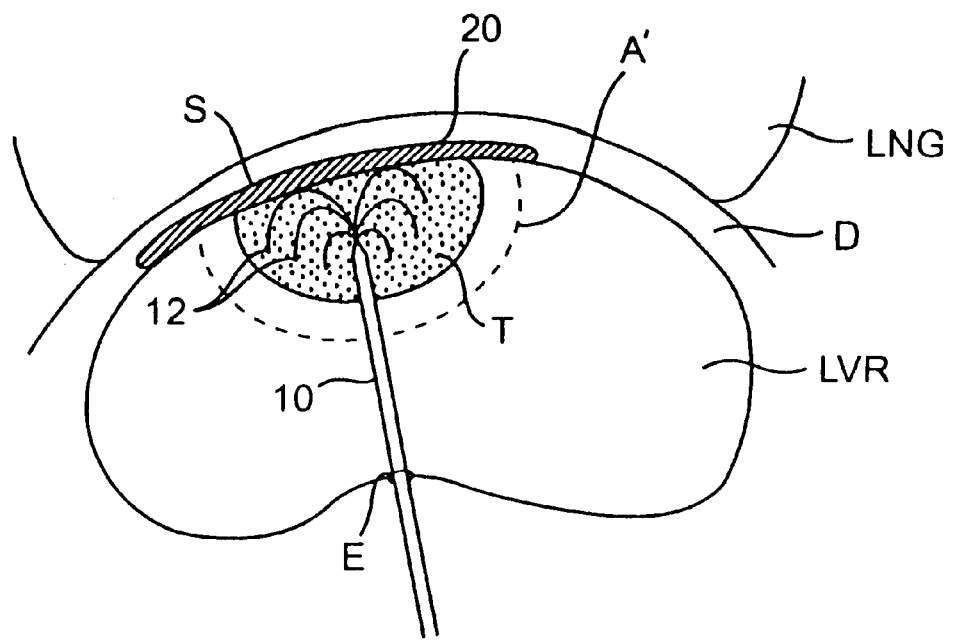
FIG. 3 illustrates the treatment of a tumor near a tissue surface with the use of the present invention to avoid difficulties illustrated in FIGS. 1–2.

Referring to FIG. 3, a tumor T may be located deep in the liver LVR, close to a back or side surface S of the organ and adjacent to the surrounding diaphragm D and/or lung LNG. The tumor T and optionally portions of surrounding tissue in the liver LVR may comprise a target region to which thermal treatment may be aimed. An interface shield 20 may be positioned over the surface S to lie between the target region or tumor T and the adjacent body tissue, in this case the diaphragm D. The tumor T may be accessed through an entry site E which is opposite this surface S, or at a location which is a considerable distance away from this surface S. As shown, a tissue penetrating or needle electrode 10, such as a LeVeen™ Needle Electrode, may be inserted through the entry point E in a direction toward the protective interface shield 20. The electrode 10 may traverse healthy liver LVR tissue and be placed such that the electrode tips 12 are located within or near the tumor T to be treated. Electrical current may then be applied to the target region through the electrode 10. Heat emanating from the tissue surrounding the electrode tips 12 may penetrate tissue within a given radius, illustrated by a dashed outlined area A'.

Figure 1:
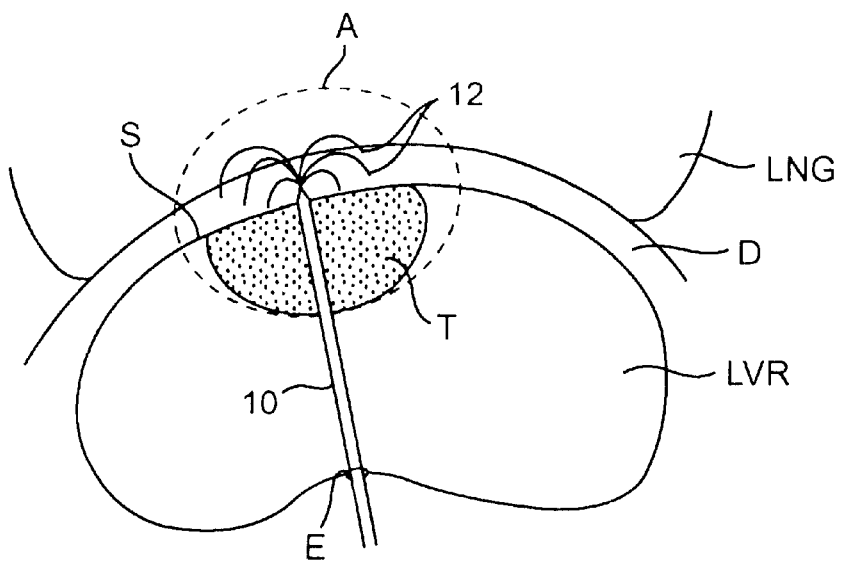
FIG. 1 illustrates the possible mistargeting a tumor near a tissue surface with a needle electrode with prior art methods.
Figure 2:
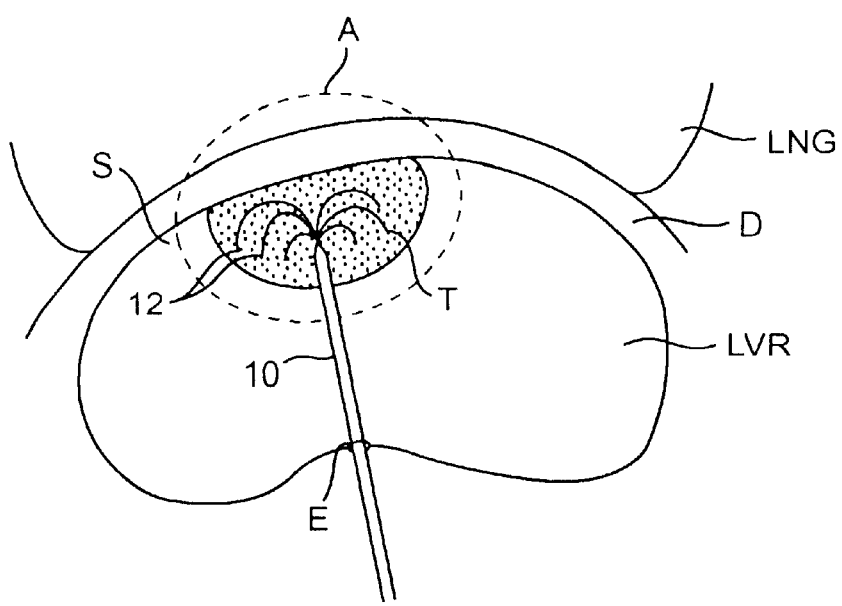
FIG. 2 illustrates possible heat emanation into adjacent tissues during hyperthermic treatment of a tumor near a tissue surface with prior art methods.

As shown in FIG. 3, the electrode 10, particularly the electrode tips 12, does not traverse the surface S and protrude into the adjacent tissue, the diaphragm D and/or lung LNG, as previously depicted in FIG. 1 (prior art). This is due to the presence and placement of the interface shield 20 over the surface S, between the target region or tumor T and the adjacent tissue. Likewise, heat emanating from the target tissue region is constrained from being conducted to the adjacent tissue, the diaphragm D and/or lung LNG. This is illustrated by a dashed outlined area A' contained within the liver LVR, in comparison to the depiction of area A in FIG. 2 (prior art). This is also due to the presence and placement of the interface shield 20 over the surface S. Thus, the shield 20 reduces the potential of at least one of (a) treatment device penetration and (b) heat transfer.

Figure 4:
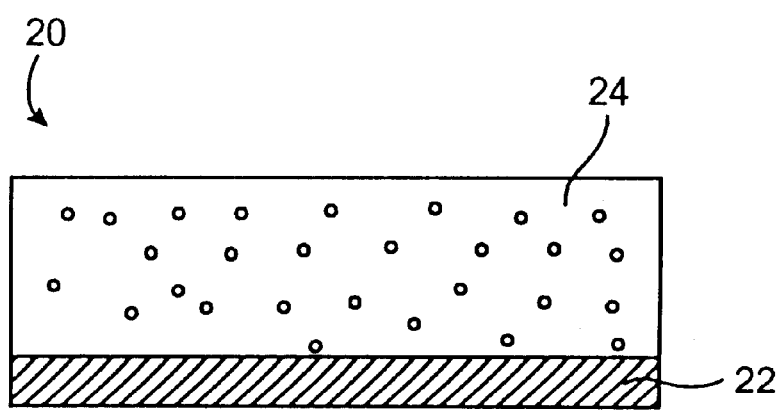
FIG. 4 is a schematic cross-sectional illustration of an interface shield having a penetration barrier and a heat transfer barrier.

In a preferred embodiment, shown in FIG. 4, the protective interface shield 20 comprises a flexible planar member having a layer which inhibits needle penetration (a penetration barrier 22) and a layer which inhibits heat transfer (a heat transfer barrier 24). The penetration barrier 22 may be comprised of any suitable penetration resistant material. For example, thin sheets of flexible nylon, fabric, or plastic, such as polyethylene terephthalate glycol comonomer (PETG), polycarbonate, polyparaphenylene (Kevlar®), and polyallomer (polyethylene polypropylene copolymer), to name a few, may be used singly, in multiple layers or in combination. The materials may be suitably resistant to penetration by a needle electrode 10, and particularly an electrode tip 12 which may be deflected along a path in a direction away from the tissues adjacent the target region. This may prevent advancement or positioning of the needle electrode 10 and/or tips 12 into adjacent tissue which is desired to be protected from such treatment. The penetration barrier 22 may be a tightly woven fabric or a continuous layer, i.e. lacking perforations or other openings or apertures, which may provide an additional benefit of inhibiting the loss of steam from the tissue which is being treated. Containment of steam within the target region further enhances tissue heating.

The heat transfer barrier 24, may be comprised of any suitable material which reduces the transfer of heat through the flexible planar member. This may be accomplished with the use of a material having a heat transfer coefficient of $8.0 \times 10^{-4}$ cal.cm/° C.cm$^2$.sec or less at 20° C. (68° F.). Thus, the material may act as a thermal insulator providing a passive barrier to heat transfer. Preferred materials are flexible and hydrophobic, or at least non-hydrophilic. Examples of such materials may include closed cell foam made from plastics, such as polyolefins (polyethylene, polyallomer, polypropylene, etc.), or from polyurethane, to name a few. Alternatively, this may be accomplished with the use of a material which absorbs heat, rather than insulates, thereby reducing the transfer of heat through the planar member. Such a material may preferentially absorb or conduct heat away from the target tissue site rather than allowing the heat to pass through. Exemplary material may undergo an endothermic phase change or chemical reaction at or above body temperature. For example, the material may be saline or a suitable fluid which is chilled or frozen and sealed in a leakproof container or membrane. Thus, the material may provide active cooling as a barrier to heat transfer.

As depicted in FIG. 4, the above described barriers 22, 24 may be arranged in layers to comprise the interface shield 20. In most cases, either side of the shield 20, the penetration barrier 22 or the heat transfer barrier 24, may be placed against the surface S of the organ within which the target tissue is located, in this example the liver LVR. However, in situations where the heat transfer barrier 24 may be damaged due to penetration by a needle electrode or other instrument, it may be preferable to position the shield 20 such that the penetration barrier 22 is against the surface S. In this manner, the heat transfer barrier 24 may be protected from any electrodes or instruments penetrating the surface S due to the presence of the penetration barrier 22. This may be particularly applicable to situations in which the heat transfer barrier 24 is comprised of a material which undergoes an endothermic phase change or chemical reaction. In the above described example, a fluid filled container or membrane may be damaged or suffer leakage if penetrated by a needle electrode. Thus, it would be desirable to position a penetration barrier 22 between the membrane and the target treatment area.

In addition to stacked layers, the above described barriers 22, 24 may be arranged in a number of patterns or configurations. For example, the heat transfer barrier 24 may encapsulate the penetration barrier 22. Such an arrangement may assist in holding the penetration barrier 22 in position, particularly if the barrier 22 is comprised of a material which is not easily bonded to the material comprising the heat transfer barrier 24. Likewise, such an arrangement may assist in holding together a number of like or dissimilar layers of material comprising the penetration barrier 22. Alternatively, the penetration barrier 22 may encapsulate the heat transfer barrier 24. Such an arrangement may aide in protecting a heat transfer barrier 24 from damage due to penetration by electrode needles or other instruments. Encapsulation may prevent piercing or penetration through any of the sides of the shield 20. Additional arrangements are possible and may be preferred in given situations.

Figure 5:
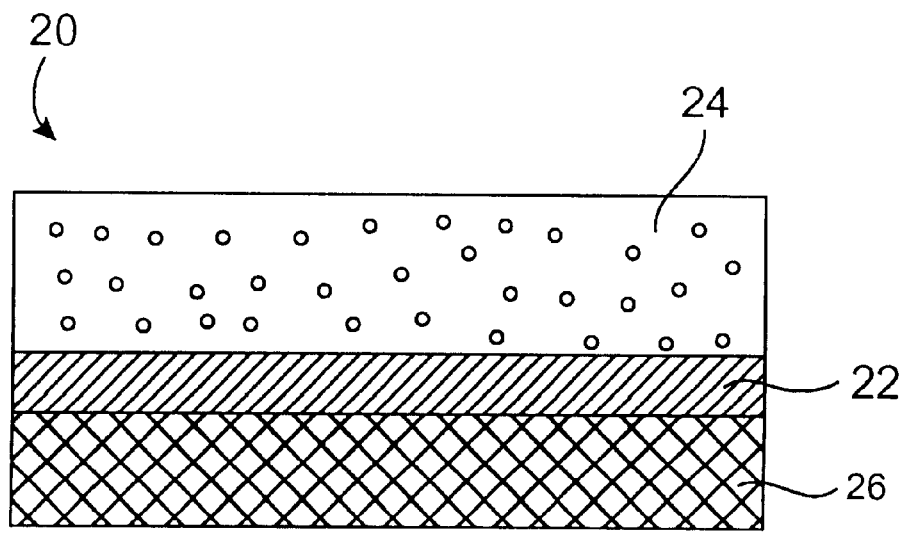
FIG. 5 is a schematic cross-sectional illustration of an interface shield having a penetration barrier, a heat transfer barrier and an electrically conductive layer.

Referring to FIG. 5, a preferred embodiment of the protective interface shield 20 comprises a flexible planar member additionally having an electrically conductive layer 26 comprised of an electrically conductive material with conductivity similar to that of body tissue. A preferred material may be hydrophilic or at least partially hydrophilic. An example of such a material may be open cell foam made from polyurethane. In general, any porous substance which holds or may hold a conductive fluid may be used despite not being itself conductive. For instance, cotton gauze or felt moist or wet with saline may be used. Alternatively, a dry material may be used which may be quickly hydrated with blood and/or other body fluids upon contact with the body tissues. The conductive layer 26 may be designed to allow radiofrequency current to leave the target treatment site in a direction towards the target tissue surface while carrying the current away from undesired non-targeted locations and tissues at the interface. The layer 26 may also be designed so that the conductance is not so high as to cause an undesired preferred current path which could inadvertently, not intentionally, distort the thermal lesion shape.

Figure 6:
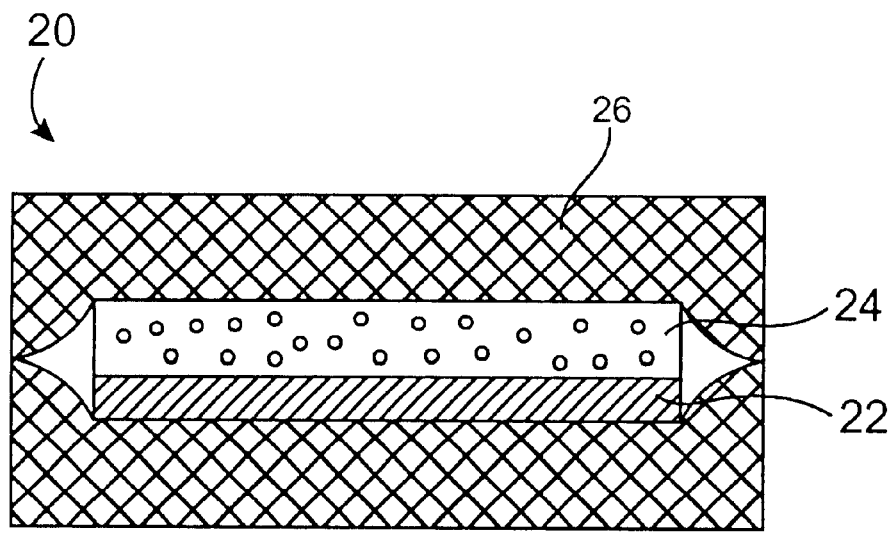
FIG. 6 is a schematic cross-sectional illustration of an interface shield having the layers illustrated in FIG. 5 in a varied arrangement.

The above described layers 22, 24, 26 may be arranged in any number of patterns or configurations, however it is preferred that the conductive layer 26 comprise a surface of the shield 20. In this manner, the conductive layer 26 may contact the surface of the organ containing the target tissue when the shield is in position. As shown in FIG. 5, the penetration barrier 22 may be surrounded by the heat transfer barrier 24 on one side of the shield 20 and the conductive layer 26 on the opposite side of the shield 20. Alternatively, as shown in FIG. 6, both the penetration barrier 22 and heat transfer barrier 24 may be encapsulated by the conductive layer 26. Additional arrangements are possible and may be preferred in given situations. Thus, any combination of the above described layers in any configuration such as to form a flexible planar member may be within the scope of the present invention.

Figure 7:
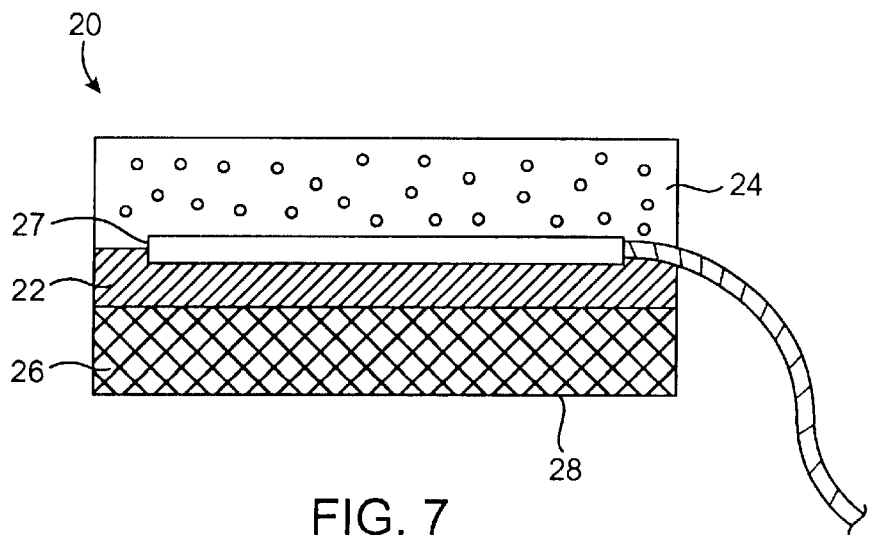
FIG. 7 is a schematic cross-sectional illustration of an interface shield having a penetration barrier, a heat transfer barrier, an electrically conductive layer and a dispersive electrode layer.

Referring to FIG. 7, a preferred embodiment of the protective interface shield 20 comprises a flexible planar member additionally having a dispersive electrode layer 27. A preferred material comprising such a layer 27 may be aluminum or copper foil. The dispersive electrode layer 27 may be designed to provide a more preferential dispersion of applied energy than the body tissues or the conductive layer 26 described above. However, it is highly desirable to avoid a "short-circuit" situation where a needle electrode or array member could make direct contact with the dispersive electrode layer so as to avoid inadvertent loss of tissue heating in the target tissue. The dispersive electrode layer 27 should therefore be isolated electrically by being encapsulated between a penetration barrier 22 and a heat transfer barrier 24. The electrically isolated dispersive electrode layer 27 will act as a capacitor to collect radiofrequency energy and return the energy to a generator or power source. Referring again to FIG. 7, a conductive layer 26 is shown on the surface of the shield 20. In addition, the dispersive electrode layer 27, which is highly conductive, is shown between the penetration barrier 22 and the heat transfer barrier 24. Preferred placement of an interface shield 20 of this design would involve positioning the shield 20 with the bottom side 28 against the surface S of the target region or tumor T. This arrangement would ensure that the heat transfer barrier 24 would lie between the dispersive electrode layer 27 and the region to be protected.

As previously described, the heat transfer barrier 24 may be an active barrier. In this case, the heat transfer barrier 24 may be comprised of a metal plate similar in size, shape and/or thickness to the dispersive electrode layer 27. The metal plate may not be electrically connected to the dispersive electrode 27 or the RF power source. Thus, the plate would serve only as an encapsulated heat conductor and not as a conductor of radiofrequency current. Spreading the heat conducted over a larger surface area may improve the efficiency of the active heat transfer barrier 24.

Figure 8:
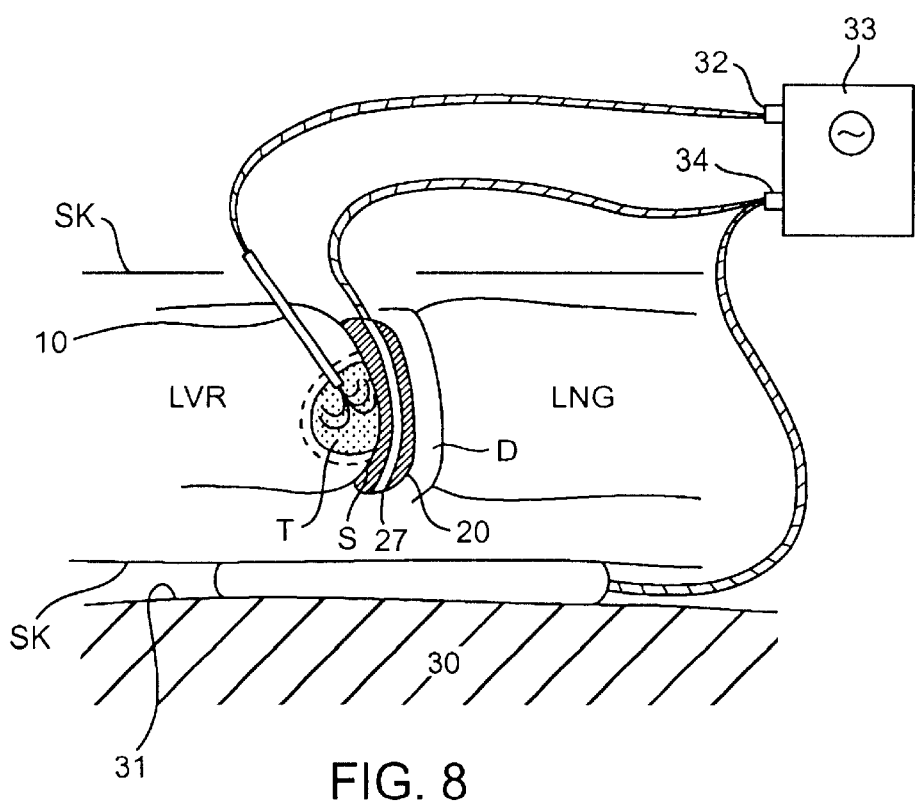
FIG. 8 is a schematic illustration of an interface shield having a dispersive electrode layer in a preferred position for use with a traditional dispersive electrode placed against the patient's skin.

Possible placement of an interface shield 20 having a dispersive electrode layer 27 is depicted in FIG. 8. The schematic illustration depicts a cross-sectional side view of a patient lying on a table 30 during treatment. A conventional dispersive electrode 31 is placed against the patient's skin SK, as shown in this illustration between the patient and the table 30. A target region or tumor T is located, in this case in the liver LVR, for hyperthermic treatment. An interface shield 20 may be positioned as shown over a surface S such that the shield 20 lies between the target region or tumor T and the adjacent body tissues, in this case the diaphragm D and lung LNG. It may be appreciated that the interface shield 20 may be placed against other surfaces of the target region or against surfaces of other organs. At least one tissue penetrating or needle electrode 10 may be introduced to the target region in a direction toward the interface shield 20. The needle electrode 10 may be electrically connected to a first output 32 of a radiofrequency power source 33. The dispersive electrode 31 may be electrically connected to a second output 34 of the power source 33, thus completing a circuit through the patient. Likewise, a dispersive electrode layer 27 in the shield 20 may also be electrically connected to the second output 34 to provide a current path parallel to the power source to the dispersive electrode 31. Although the use of a dispersive electrode 31 is preferred when using a shield comprising a dispersive electrode layer 27, such a shield may be used alone without the dispersive electrode 31 on the patient's skin SK, particularly if a thermal lesion offset towards the shield is desired. In either case, heating may occur in the target region for effective hyperthermic treatment while adjacent tissues body tissues D, LNG may be protected from such effects due to various features of the shield described above.

Figure 9:
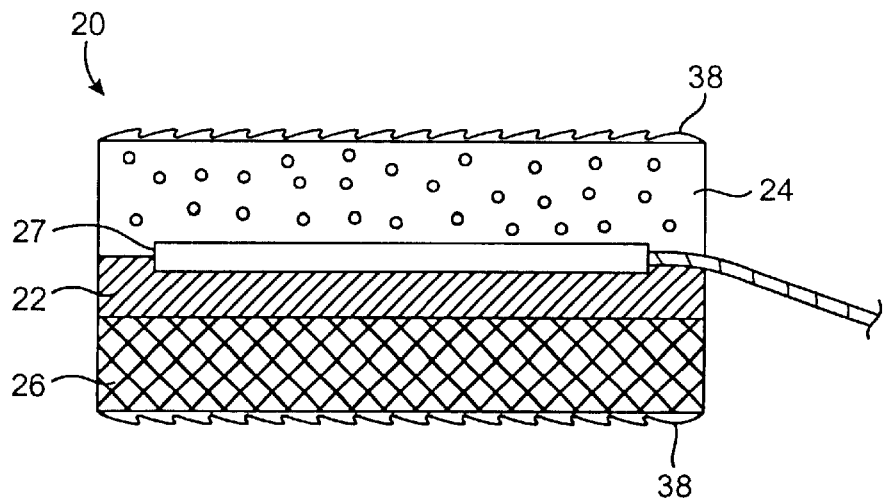
FIG. 9 is a schematic cross-sectional illustration of an interface shield having a penetration barrier, a heat transfer barrier, an electrically conductive layer and a surface coating or layer.

Referring to FIG. 9, the protective interface shield 20 may have inherent surface characteristics, or a surface coating or surface layer 38 to provide desired surface characteristics for specific purposes. For example, a non-sliding surface may be desired to enhance placement stability of the shield 20 against the organ containing the target tissue to be treated. In this case, the surface layer 38 may be comprised of felt or a coarsely woven fabric material which reduces movement between the shield 20 and the surface area of the body organ over which the shield 20 is positioned. Such a surface layer 38 may be located on one side of the shield 20, it may be located on both sides of the shield 20, as shown in FIG. 9, it may encapsulate the shield 20, or it may be located on various sub-portions of the shield 20. Alternatively, it may be desired that the surface layer 38 provide a low friction interface between the shield 20 and contacting tissue. This may be particularly applicable to the portion of the shield 20 in contact with the adjacent tissues. The low friction may allow adequate movement between the shield 20 and the adjacent tissue, such as the diaphragm D or lung LNG which may be moving relative to the target volume during the procedure. Such a surface layer 38 may therefore reduce irritation to the contacting tissues. Thus, a variety of surface layers 38 may be applicable for different purposes and may be combined in any number of patterns or configurations on the shield 20 to provide the desired characteristics. In a preferred embodiment, the shield 20 may comprise a non-slip surface on one side of the shield 20, for placement against the target organ, and a relatively frictionless surface on the opposite side of the shield 20, for contact against the moving adjacent tissues. In this case, the surface layer may comprise a first portion located on a first side of the interface shield, wherein the first side inhibits movement between the flexible planar member and the target tissue, and a second portion located on a second side opposite the first side of the interface shield, wherein the second side permits movement between the flexible planar member and the adjacent body tissue. In this example, the first side may be comprised of a woven fabric material and the second side may be comprised of a lubricious coating.

As described above, the protective interface shield may be comprised of layers or materials which provide one or more of the following properties: a) penetration barrier, b) heat transfer barrier, c) electrical conduction, d) dispersive electrode and e) surface characteristics. For illustrative purposes, it has generally been described that each of these properties are provided by separate layers or materials, or a combination of materials. However, it may be appreciated that more than one property may be provided by a specific layer or material. For example, an interface shield may be comprised of a dual layer, wherein the dual layer comprises a penetration barrier and a heat transfer barrier. Or, the dual layer may comprise a penetration barrier and an electrically conductive layer. Likewise, a material which provides a penetration barrier may also provide a barrier to heat transfer and have different surface textures on each side. If an interface shield were to be comprised of this material, the shield may be comprised of a single layer yet provide three or even four properties. This may be extrapolated to all materials which may be used to comprise such a shield, and therefore the present invention is not limited to specific numbers of layers.

Figure 10:
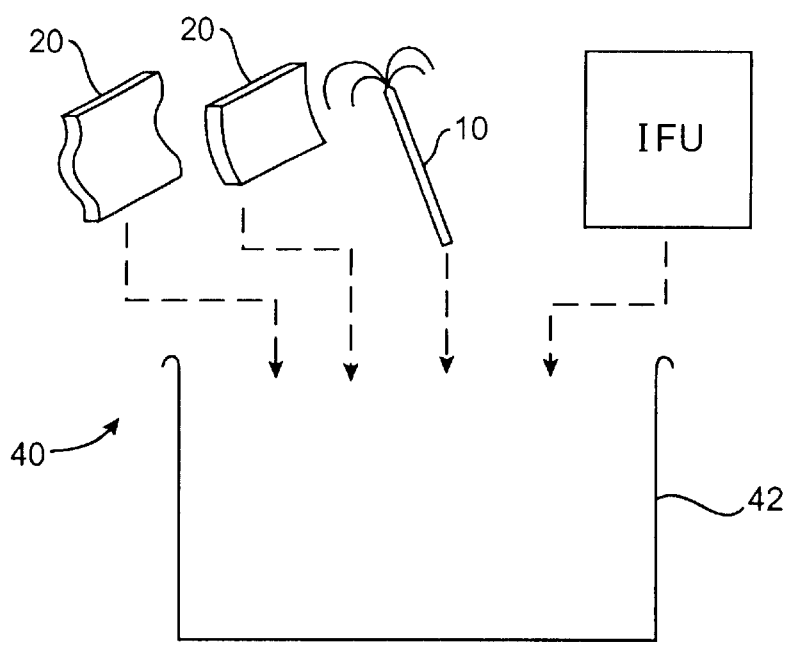
FIG. 10 illustrates a kit constructed in accordance with the principles of the present invention.

Referring to FIG. 10, kits 40 according to the present invention comprise at least one interface shield 20 and instructions for use IFU. Optionally, the kits may further include additional shields 20, as shown. These shields 20 may be identical or may differ in size, shape, composition, arrangement or properties provided, for example. The shields may interlock to cover a larger contiguous area or to implement stacking. Such kits may further include a tissue penetrating electrode 10 and any other materials or items relevant to the present invention. The instructions for use IFU will set forth any of the methods as described above, and all kit components will usually be packaged together in a pouch 42 or other conventional medical device packaging. Usually, those kit components used in performing the procedure on the patient will be sterilized and maintained within the kit. Optionally, separate pouches, bags, trays or other packaging may be provided within a larger package, where the smaller packs may be opened separately to separately maintain the components in a sterile fashion.

Although the forgoing invention has been described in some detail by way of illustration and example, for purposes of clarity of understanding, it will be obvious that various alternatives, modifications and equivalents may be used and the above description should not be taken as limiting in scope of the invention which is defined by the appended claims.

What is claimed is:

1. An interface shield for protecting an adjacent body tissue during thermal treatment of a target tissue within a body of a patient, said shield comprising:
a flexible planar member having a first layer and a second layer, wherein the first layer comprises a penetration barrier and the second layer comprises a heat transfer barrier when positioned against a surface of a target tissue, wherein the penetration barrier is comprised of a material having a Charpy or Izod toughness of at least 10 cm-kg/cm (2.0 ft-lbf/in).

2. An interface shield as in claim 1, wherein the penetration barrier material is selected from the group consisting of nylon, polyallomer, polyethylene terephthalate glycol comonomer, polycarbonate, plastic, and polyparaphenylene.

3. An interface shield as in claim 1, wherein the heat transfer barrier comprises a material having a heat transfer coefficient of $8.0\times10^{-4}$ cal.cm/° C.cm$^2$.sec or less at 20° C. (68° F.).

4. An interface shield as in claim 3, wherein the heat transfer barrier comprises a material which is at least partially non-hydrophilic.

5. An interface shield as in claim 4, wherein the heat transfer barrier comprises a material which is hydrophobic.

6. An interface shield as in claim 4, wherein the heat transfer barrier comprises closed cell foam or open cell foam.

7. An interface shield as in claim 1, wherein the heat transfer barrier comprises a material that absorbs heat.

8. An interface shield as in claim 7, wherein the heat absorbing material can undergo an endothermic phase change or endothermic chemical reaction at or above body temperature.

9. An interface shield as in claim 1, wherein the heat transfer barrier comprises a material that conducts heat away from the target tissue.

10. An interface shield as in claim 9, wherein the heat conducting material comprises a metallic sheet.

11. An interface shield as in claim 9, wherein the heat conducting material comprises an encapsulated thermally conductive fluid.

12. An interface shield as in claim 1, further comprising an electrically conductive layer.

13. An interface shield as in claim 12, wherein the electrically conductive layer comprises a material which is at least partially hydrophilic.

14. An interface shield as in claim 12, wherein the electrically conductive layer comprises a porous substrate capable of absorbing a conductive fluid.

15. An interface shield as in claim 14, wherein the conductive fluid comprises saline, blood and/or body fluids.

16. An interface shield as in claim 1, further comprising a dispersive electrode layer which acts as a dispersive electrode when connected to a current source.

17. An interface shield as in claim 16, wherein the dispersive electrode layer acts as a dispersive electrode when connected to a current source in parallel with a dispersive electrode on a surface of the body of the patient.

18. An interface shield as in claim 16, wherein the heat transfer barrier lies between the dispersive electrode layer and the adjacent body tissue.

19. An interface shield as in claim 16, wherein the dispersive electrode layer lies between non-electrically conductive layers so that the dispersive electrode layer in combination with the adjacent body tissue acts as a capacitor when electrical current is applied.

20. A interface shield as in claim 19, wherein the dispersive electrode layer comprises a metallic sheet or an electrically conductive fluid.

21. An interface shield as in claim 1, further comprising a surface layer.

22. An interface shield as in claim 21, wherein the surface layer inhibits relative movement between the flexible planar member and a body organ.

23. An interface shield as in claim 22, wherein the surface layer comprises gauze or felt.

24. An interface shield as in claim 21, wherein the surface layer permits relative movement between the flexible planar member and the adjacent body tissue.

25. An interface shield as in claim 21, wherein the surface layer comprises the heat transfer barrier.

26. An interface shield as in claim 25, wherein the surface layer comprises a smooth polyethylene foam or a heat absorbing or conducting material coated with a hydrophilic material.

27. An interface shield as in claim 21, wherein the surface layer inhibits movement between the flexible planar member and the target tissue and permits movement between the flexible planar member and the adjacent body tissue.

28. An interface shield as in claim 27, wherein the surface layer comprises a first portion located on a first side of the interface shield, wherein the first side comprises a woven fabric material which inhibits movement between the flexible planar member and the target tissue, and a second portion located on a second side opposite the first side of the interface shield, wherein the second side comprises a lubricious coating which permits movement between the flexible planar member and the adjacent body tissue.

29. An interface shield as in claim 1, wherein the target tissue comprises a liver and the adjacent body tissue comprises a diaphragm.

30. An interface shield as in claim 1, wherein the flexible planar member has an area in the range from 50 cm$^2$ to 300 cm$^2$.

31. An interface shield for protecting an adjacent body tissue during thermal treatment of a target tissue within a body of a patient, said shield comprising:
a flexible planar member having a first layer and a second layer, wherein the first layer comprises a penetration barrier and the second layer comprises a heat transfer barrier when positioned against a surface of a target tissue, wherein the heat transfer barrier comprises a material having a heat transfer coefficient of $8.0\times10^{-4}$ cal.cm/° C.cm$^2$.sec or less at 20° C. (68° F.).

32. An interface shield as in claim 31, wherein the penetration barrier is comprised of a material having a Charpy or Izod toughness of at least 10 cm-kg/cm (2.0 ft-lbf/in).

33. An interface shield as in claim 32, wherein the material is selected from the group consisting of nylon, polyallomer, polyethylene terephthalate glycol comonomer, polycarbonate, plastic, and poly-paraphenylene.

34. An interface shield as in claim 31, wherein the heat transfer barrier comprises a material which is at least partially non-hydrophilic.

35. An interface shield as in claim 34, wherein the heat transfer barrier comprises a material which is hydrophobic.

36. An interface shield as in claim 34, wherein the heat transfer barrier comprises closed cell foam or open cell foam.

37. An interface shield as in claim 31, wherein the heat transfer barrier comprises a material that absorbs heat.

38. An interface shield as in claim 37, wherein the heat absorbing material can undergo an endothermic phase change or endothermic chemical reaction at or above body temperature.

39. An interface shield as in claim 29, wherein the heat transfer barrier comprises a material that conducts heat away from the target tissue.

40. An interface shield as in claim 39, wherein the heat conducting material comprises a metallic sheet.

41. An interface shield as in claim 39, wherein the heat conducting material comprises an encapsulated thermally conductive fluid.

42. An interface shield as in claim 24, further comprising an electrically conductive layer.

43. An interface shield as in claim 42, wherein the electrically conductive layer comprises a material which is at least partially hydrophilic.

44. An interface shield as in claim 42, wherein the electrically conductive layer comprises a porous substrate capable of absorbing a conductive fluid.

45. An interface shield as in claim 44, wherein the conductive fluid comprises saline, blood and/or body fluids.

46. An interface shield as in claim 28, further comprising a dispersive electrode layer which acts as a dispersive electrode when connected to a current source.

47. An interface shield as in claim 46, wherein the dispersive electrode layer acts as a dispersive electrode when connected to a current source in parallel with a dispersive electrode on a surface of the body of the patient.

48. An interface shield as in claim 46, wherein the heat transfer barrier lies between the dispersive electrode layer and the adjacent body tissue.

49. An interface shield as in claim 46, wherein the dispersive electrode layer lies between non-electrically conductive layers so that the dispersive electrode layer in combination with the adjacent body tissue acts as a capacitor when electrical current is applied.

50. A interface shield as in claim 49, wherein the dispersive electrode layer comprises a metallic sheet or an electrically conductive fluid.

51. An interface shield as in claim 31, further comprising a surface layer.

52. An interface shield as in claim 31, wherein the surface layer inhibits relative movement between the flexible planar member and a body organ.

53. An interface shield as in claim 52, wherein the surface layer comprises gauze or felt.

54. An interface shield as in claim 51, wherein the surface layer permits relative movement between the flexible planar member and the adjacent body tissue.

55. An interface shield as in claim 51, wherein the surface layer comprises the heat transfer barrier.

56. An interface shield as in claim 55, wherein the surface layer comprises a smooth polyethylene foam or a heat absorbing or conducting material coated with a hydrophilic material.

57. An interface shield as in claim 51, wherein the surface layer inhibits movement between the flexible planar member and the target tissue and permits movement between the flexible planar member and the adjacent body tissue.

58. An interface shield as in claim 57, wherein the surface layer comprises a first portion located on a first side of the interface shield, wherein the first side comprises a woven fabric material which inhibits movement between the flexible planar member and the target tissue, and a second portion located on a second side opposite the first side of the interface shield, wherein the second side comprises a lubricious coating which permits movement between the flexible planar member and the adjacent body tissue.

59. An interface shield as in claim 31, wherein the target tissue comprises a liver and the adjacent body tissue comprises a diaphragm.

60. An interface shield as in claim 31, wherein the flexible planar member has an area in the range from 50 cm$^2$ to 300 cm$^2$.

61. An interface shield for protecting an adjacent body tissue during thermal treatment of a target tissue within a body of a patient, said shield comprising:

a flexible planar member having a first layer and a second layer, wherein the first layer comprises a penetration barrier and the second layer comprises a heat transfer barrier when positioned against a surface of a target tissue; and a dispersive electrode layer which acts as a dispersive electrode when connected to a current source in parallel with a dispersive electrode on a surface of the body of the patient.

62. An interface shield as in claim 61, wherein the penetration barrier is comprised of a material having a Charpy or Izod toughness of at least 10 cm-kg/cm (2.0 ft-lbf/in).

63. An interface shield as in claim 62, wherein the material is selected from the group consisting of nylon, polyallomer, polyethylene terephthalate glycol comonomer, polycarbonate plastic, and poly-paraphenylene.

64. An interface shield as in claim 61, wherein the heat transfer barrier comprises a material having a heat transfer coefficient of $8.0 \times 10^{-4}$ cal.cm/° C.cm$^2$.sec or less at 20° C. (68° F.).

65. An interface shield as in claim 64, wherein the heat transfer barrier comprises a material which is at least partially non-hydrophilic.

66. An interface shield as in claim 65, wherein the heat transfer barrier comprises a material which is hydrophobic.

67. An interface shield as in claim 65, wherein the heat transfer barrier comprises closed cell foam or open cell foam.

68. An interface shield as in claim 61, wherein the heat transfer barrier comprises a material that absorbs heat.

69. An interface shield as in claim 68, wherein the heat absorbing material can undergo an endothermic phase change or endothermic chemical reaction at or above body temperature.

70. An interface shield as in claim 61, wherein the heat transfer barrier comprises a material that conducts heat away from the target tissue.

71. An interface shield as in claim 70, wherein the heat conducting material comprises a metallic sheet.

72. An interface shield as in claim 70, wherein the heat conducting material comprises an encapsulated thermally conductive fluid.

73. An interface shield as in claim 61, further comprising an electrically conductive layer.

74. An interface shield as in claim 73, wherein the electrically conductive layer comprises a material which is at least partially hydrophilic.

75. An interface shield as in claim 73, wherein the electrically conductive layer comprises a porous substrate capable of absorbing a conductive fluid.

76. An interface shield as in claim 75, wherein the conductive fluid comprises saline, blood and/or body fluids.

77. An interface shield as in claim 61, wherein the heat transfer barrier lies between the dispersive electrode layer and the adjacent body tissue.

78. An interface shield as in claim 61, wherein the dispersive electrode layer lies between non-electrically conductive layers so that the dispersive electrode layer in combination with the adjacent body tissue acts as a capacitor when electrical current is applied.

79. A interface shield as in claim 78, wherein the dispersive electrode layer comprises a metallic sheet or an electrically conductive fluid.

80. An interface shield as in claim 61, further comprising a surface layer.

81. An interface shield as in claim 80, wherein the surface layer inhibits relative movement between the flexible planar member and a body organ.

82. An interface shield as in claim 81, wherein the surface layer comprises gauze or felt.

83. An interface shield as in claim 80, wherein the surface layer permits relative movement between the flexible planar member and the adjacent body tissue.

84. An interface shield as in claim 80, wherein the surface layer comprises the heat transfer barrier.

85. An interface shield as in claim 84, wherein the surface layer comprises a smooth polyethylene foam or a heat absorbing or conducting material coated with a hydrophilic material.

86. An interface shield as in claim 80, wherein the surface layer inhibits movement between the flexible planar member and the target tissue and permits movement between the flexible planar member and the adjacent body tissue.

87. An interface shield as in claim 86, wherein the surface layer comprises a first portion located on a first side of the interface shield, wherein the first side comprises a woven fabric material which inhibits movement between the flexible planar member and the target tissue, and a second portion located on a second side opposite the first side of the interface shield, wherein the second side comprises a lubricious coating which permits movement between the flexible planar member and the adjacent body tissue.

88. An interface shield as in claim 61, wherein the target tissue comprises a liver and the adjacent body tissue comprises a diaphragm.

89. An interface shield as in claim 61, wherein the flexible planar member has an area in the range from 50 $cm^2$ to 300 $cm^2$.

* * * * *